US007316813B2

(12) United States Patent
Eichhorn

(10) Patent No.: US 7,316,813 B2
(45) Date of Patent: Jan. 8, 2008

(54) INFLUENZA VACCINE COMPOSITION

(75) Inventor: Uwe Eichhorn, Dresden (DE)

(73) Assignee: Saechsisches Serumwerk Dresden Branch of SmithKline Beecham Pharma GmbH & Co KG, Dresden (DE)

( * ) Notice: Subject to any disclaimer, the term of this patent is extended or adjusted under 35 U.S.C. 154(b) by 0 days.

(21) Appl. No.: 10/480,952

(22) PCT Filed: May 29, 2002

(86) PCT No.: PCT/EP02/05883

§ 371 (c)(1),
(2), (4) Date: Jun. 22, 2004

(87) PCT Pub. No.: WO02/097072

PCT Pub. Date: Dec. 5, 2002

(65) Prior Publication Data

US 2004/0241187 A1 Dec. 2, 2004

(30) Foreign Application Priority Data

May 30, 2001 (GB) ................................ 0113083.0
Feb. 21, 2002 (GB) ................................ 0204116.8

(51) Int. Cl.
*A61K 39/145* (2006.01)

(52) U.S. Cl. .............................. 424/210.1; 424/204.1; 424/205.1; 424/206.1; 424/209.1

(58) Field of Classification Search ............ 424/204.1, 424/205.1, 206.1, 209.1, 210.1; 435/238
See application file for complete search history.

(56) References Cited

U.S. PATENT DOCUMENTS 5,472,706 A * 12/1995 Friedman et al. ........... 424/450
5,616,487 A 4/1997 Eisfeld et al.
5,919,480 A 7/1999 Yechezkel et al.
6,156,297 A 12/2000 Mellul et al.

FOREIGN PATENT DOCUMENTS

| | | |
|---|---|---|
| DE | 195 47 160 | 6/1997 |
| EP | 0 400 569 | 12/1990 |
| EP | 0 750 907 | 1/1997 |
| EP | 0 985 408 | 3/2000 |
| WO | WO95/11700 | 5/1995 |
| WO | WO98/24409 | 6/1998 |
| WO | WO98/30228 | 7/1998 |
| WO | WO98/42373 | 10/1998 |
| WO | WO98/56414 | 10/1998 |
| WO | WO98/56414 | * 12/1998 |
| WO | WO99/11241 | 3/1999 |
| WO | WO99/52549 | 10/1999 |
| WO | WO 01/08495 | 2/2001 |
| WO | WO 01/14411 | 3/2001 |
| WO | WO 01/28552 | 4/2001 |
| WO | WO 02/28426 | 4/2002 |

OTHER PUBLICATIONS

MMWR Recomm Rep. Apr. 30, 1999;48(RR-4):1-28 [No authors listed], Table 1 only.*
Ball et al, "An assessment of thimerosal use in childhood vaccines", Pediatrics, vol. 107, No. 5, May 2001 pp. 1147-1154.
Bernard et al., "Autism: A novel of mercury poisioning", Medical Hypotheses, vol. 56, No. 4, Apr. 2001, pp. 462-471.
Brown et al., "Vaccinator device for delivery propellant-driven aerosols of *Streptococcus suis* bacterin into the respiratory tracts of swine", Vaccine, Butterworth Scientific, Guildford, GB, vol. 15, No. 11, Aug. 1, 1997, pp. 1165-1173.
Ellis, "Technologies for the design, discovery, formulation and administration of vaccines", Vaccine, Butterworth Scientific, Guildford, GB, vol. 19, No. 17-19, Mar. 21, 2001, pp. 2681-2687.
Goetsch et al., "BBG2Na an RSV subunit vaccine candidate intramuscularly injected to human confers protection against viral challenge after nasal immunication in mice", Vaccine, Butterworth Scientific Guildford, GB, vol. 19, No. 28-29, Jul. 16, 2001, pp. 4036-4042.
Newman et al., "Use of nonionic block copolymers in vaccines and therapeutics", Critical Reviews in Therapeutic Drug Carrier Systems, United States 1998, vol. 15, No. 2, 1998, pp. 89-142.
Ott et al., "Enhancement of humoral response against human influenza vaccine with the simple submicron oil/water emulsion adjuvant MF59", Vaccine, Butterworth Scientific., Guildford, GB, vol. 13, No. 16, Nov. 1, 1995, pp. 1557-1562.
Porschmann et al., "Application of surfactants to the supercritical fluid extraction of nitroaromatic compounds from sediments", Journal of Chromatography A, Elsevier Science, NL, vol. 816, No. 2, Aug. 14, 1998, pp. 221-232.
Poryvaev et al., "The effect of conditions of storage and composition of viral material on lipid peroxidation of the viral envelope and inactivation of the invluenza virus", *Voprosy virusologii*, Russia, vol. 40, pp. 62-65, 1995.

* cited by examiner

*Primary Examiner*—Bruce R. Campell
*Assistant Examiner*—Myron G. Hill
(74) *Attorney, Agent, or Firm*—Elizabeth J. Hecht; Edward R. Gimmi; Charles M. Kinzig

(57) ABSTRACT

An inactivated influenza virus preparation is described which comprises a haemagglutinin antigen stabilized in the absence of thiomersal, or at low levels of thiomersal, wherein the haemagglutinin is detectable by a SRD assay. The influenza virus preparation may comprise a micelle modifying excipient, for example α-tocopherol or a derivative thereof in a sufficient amount to stabilize the haemagglutinin.

16 Claims, 2 Drawing Sheets

Group 1: 2 IN Primings;Thio+Ag
Group 2: 2 IN Primings;Thio Red
Group 3: 1 IN Primings;Thio Red
Group 4: 2 IN Primings;Thio Red
Group 5: 1 IN Primings;Thio Red
Group 6: 2 IN Primings;Thio Red

INFLUENZA VACCINE COMPOSITION

This application is a National Stage Entry of PCT/EP02/05883, filed May 29, 2002.

This invention relates to novel influenza virus antigen preparations, methods for preparing them and their use in prophylaxis or therapy. In particular the invention relates to inactivated influenza vaccines which are disrupted rather than whole virus vaccines and which are stable in the absence of organomercurial preservatives. Moreover, the vaccines contain haemagglutinin which is stable according to standard tests. The vaccines can be administered by any route suitable for such vaccines, such as intramuscularly, subcutaneously, intradermally or mucosally e.g. intranasally.

Influenza virus is one of the most ubiquitous viruses present in the world, affecting both humans and livestock. The economic impact of influenza is significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. The surface glycoproteins neuraminidase (NA) and haemagglutinin (HA) appear as spikes, 10 to 12 nm long, at the surface of the particles. It is these surface proteins, particularly the haemagglutinin, that determine the antigenic specificity of the influenza subtypes.

Currently available influenza vaccines are either inactivated or live attenuated influenza vaccine, Inactivated flu vaccines are composed of three possible forms of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are given intramuscularly (i.m.) or intranasally (i.n.). There is no commercially available live attenuated vaccine.

Influenza vaccines, of all kinds, are usually trivalent vaccines. They generally contain antigens derived from two influenza A virus strains and one influenza B strain. A standard 0.5 ml injectable dose in most cases contains 15 μg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330).

The influenza virus strains to be incorporated into influenza vaccine each season are determined by the World Health Organisation in collaboration with national health authorities and vaccine manufacturers.

Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease. These groups in particular therefore need to be protected.

Current efforts to control the morbidity and mortality associated with yearly epidemics of influenza are based on the use of intramuscularly administered inactivated influenza vaccines. The efficacy of such vaccines in preventing respiratory disease and influenza complications ranges from 75% in healthy adults to less than 50% in the elderly.

Standards are applied internationally to measure the efficacy of influenza vaccines. The European Union official criteria for an effective vaccine against influenza are set out in the table below. Theoretically, to meet the European Union requirements, an influenza vaccine has to meet only one of the criteria in the table, for all strains of influenza included in the vaccine. However in practice, at least two or all three of the criteria will need to be met for all strains, particularly for a new vaccine such as a new vaccine for delivery via a different route. Under some circumstances two criteria may be sufficient. For example, it may be acceptable for two of the three criteria to be met by all strains while the third criterion is met by some but not all strains (e.g. two out of three strains). The requirements are different for adult populations (18-60 years) and elderly populations (>60 years).

| | 18–60 years | >60 years |
|---|---|---|
| Seroconversion rate* | >40% | >30% |
| Conversion factor** | >2.5 | >2.0 |
| Protection rate*** | >70% | >60% |

*Seroconversion rate is defined as the percentage of vaccinees who have at least a 4-fold increase in serum haemagglutinin inhibition (HI) titres after vaccination, for each vaccine strain.

**Conversion factor is defined as the fold increase in serum HI geometric mean titres (GMTs) after vaccination, for each vaccine strain.

***Protection rate is defined as the percentage of vaccinees with a serum HI titre equal to or greater than 1:40 after vaccination (for each vaccine strain) and is normally accepted as indicating protection.

For a novel flu vaccine to be commercially useful it will not only need to meet those standards, but also in practice it will need to be at least as efficacious as the currently available injectable vaccines. It will also need to be commercially viable in terms of the amount of antigen and the number of administrations required.

The current commercially available influenza vaccines are either split or subunit injectable vaccines. These vaccines are prepared by disrupting the virus particle, generally with an organic solvent or a detergent, and separating or purifying the viral proteins to varying extents. Split vaccines are prepared by fragmentation of whole influenza virus, either infectious or inactivated, with solubilizing concentrations of organic solvents or detergents and subsequent removal of the solubilizing agent and some or most of the viral lipid material. Split vaccines generally contain contaminating matrix protein and nucleoprotein and sometimes lipid, as well as the membrane envelope proteins. Split vaccines will usually contain most or all of the virus structural proteins although not necessarily in the same proportions as they occur in the whole virus. Subunit vaccines on the other hand consist essentially of highly purified viral surface proteins, haemagglutinin and neuraminidase, which are the surface proteins responsible for eliciting the desired virus neutralising antibodies upon vaccination.

Many vaccines which are currently available require a preservative to prevent deterioration. A frequently used preservative is thimerosal which is a mercury-containing compound. Some public concerns have been expressed about the effects of mercury containing compounds. There is no surveillance system in place to detect the effects of low to moderate doses of organomercurials on the developing nervous system, and special studies of children who have received high doses of organomercurials will take several years to complete. Certain commentators have stressed that the potential hazards of thimerosal-containing vaccines should not be overstated (Offit; P.A. JAMA Vol. 283; No: 16). Nevertheless, it would be advantageous to find alternative methods for the preparation of vaccines to replace the use of thiomerosal in the manufacturing process. There is thus a need to develop vaccines which are thimerosal-free, in particular vaccines like influenza vaccines which are recommended, at least for certain population groups, on an annual basis.

It has been standard practice to date to employ a preservative for commercial inactivated influenza vaccines, during the production/purification process and/or in the final vaccine. The preservative is required to prevent microorganisms from growing through the various stages of purification. For egg-derived influenza vaccines, thiomersal is typically added to the raw allantoic fluid and may also be added a second time during the processing of the virus. Thus there will be residual thiomersal present at the end of the process, and this may additionally be adjusted to a desirable preservative concentration in the final vaccine, for example to a concentration of around 100 μg/ml.

A side-effect of the use of thiomersal as a preservative in flu vaccines is a stabilisation effect. The thiomersal in commercial flu vaccines acts to stabilise the HA component of the vaccine, in particular but not exclusively HA of B strain influenza. Certain A strain haemagglutinins e.g. H3 may also require stabilisation. Therefore, although it may be desirable to consider removing thiomersal from influenza vaccines, or at least reducing the concentration of the thiomersal in the final vaccine, there is a problem to overcome in that, without thiomersal, the HA will not be sufficiently stable.

It has been discovered in the present invention that it is possible to stabilise HA in inactivated influenza preparations using alternative reagents that do not contain organomercurials. The HA remains stabilised such that it is detectable over time by quantitative standard methods, in particular SRD, to an greater extent than a non-stabilised antigen preparation produced by the same method but without stabilising excipient. The SRD method is performed as described hereinabove. Importantly, the HA remains stabilised for up to 12 months which is the standard required of a final flu vaccine.

Figure 1:
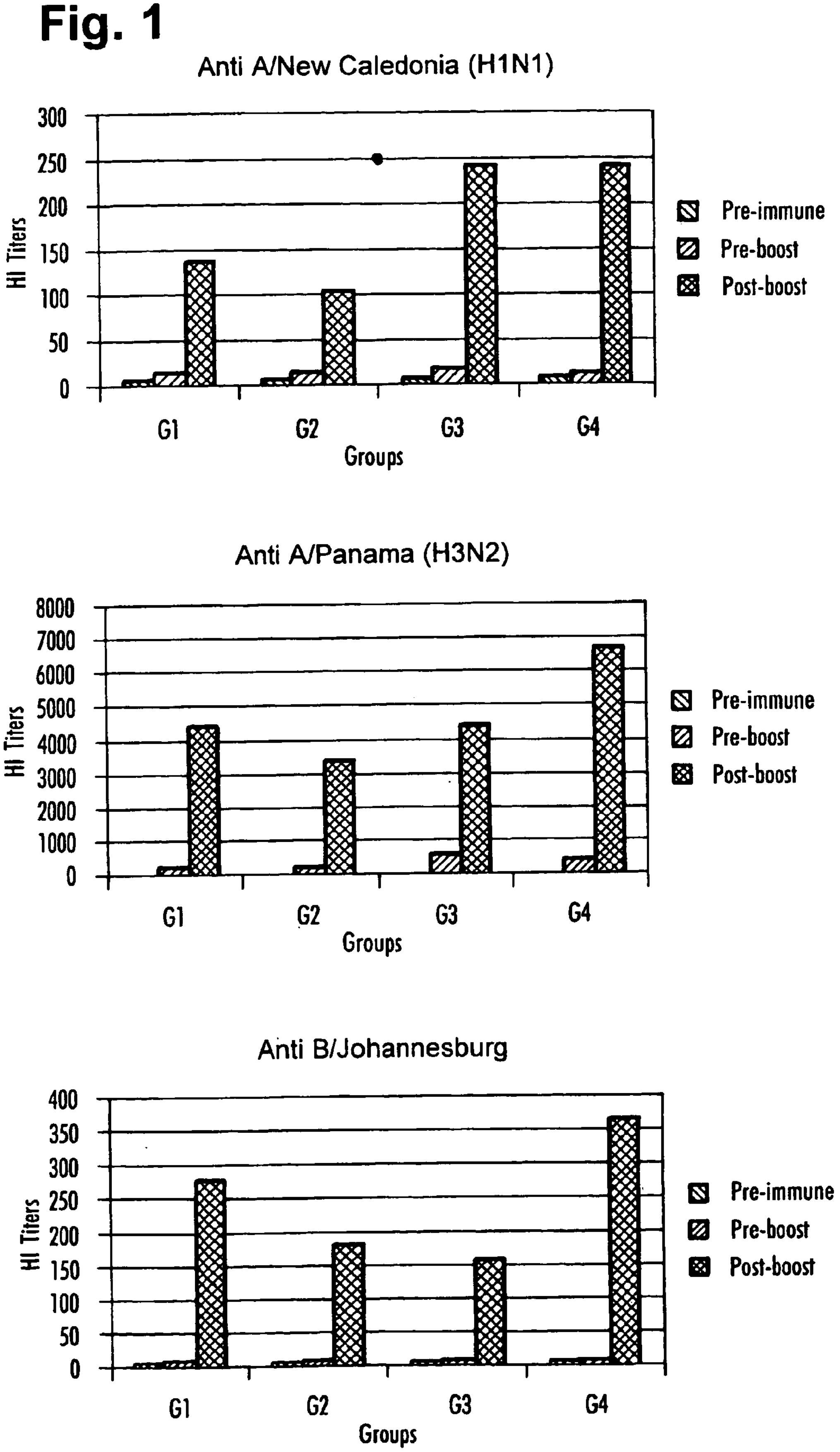
FIG. 1 is the results of the HI (haemagglutinin inhibition) assay done in Example 10.

In a first aspect the present invention provides an inactivated influenza virus preparation comprising a haemagglutinin antigen stabilised in the absence of thiomersal, or at low levels of thiomersal, wherein the haemagglutinin is detectable by a SRD assay.

Low levels of thiomersal are those levels at which the stability of HA derived from influenza B is reduced, such that a stabilising excipient is required for stabilised HA. Low levels of thiomersal are generally 5 μg/ml or less.

Generally, stabilised HA refers to HA which is detectable over time by quantitative standard methods, in particular SRD, to a greater extent than a non-stabilised antigen preparation produced by the same method but without any stabilising excipient. Stabilisation of HA preferably maintains the activity of HA substantially constant over a one year period. Preferably, stabilisation allows the vaccine comprising HA to provide acceptable protection after a 6 month storage period, more preferably a one year period.

Suitably, stabilisation is carried out by a stabilising excipient, preferably a micelle modifying excipient. A micelle modifying excipient is generally an excipient that may be incorporated into a micelle formed by detergents used in, or suitable for, solubilising the membrane protein HA, such as the detergents Tween 80, Triton X100 and deoxycholate, individually or in combination.

Without wishing to be constrained by theory, it is believed that the excipients work to stabilise HA by interaction with the lipids, detergents and/or proteins in the final preparation. Mixed micelles of excipient with protein and lipid may be formed, such as micelles of Tween and deoxycholate with residual lipids and/or Triton X-100. It is thought that surface proteins are kept solubilised by those complex micelles. Preferably, protein aggregation is limited by charge repulsion of micelles containing suitable excipients, such as micelles containing negatively charged detergents.

Suitable micelle modifying excipients include: positively, negatively or zwitterionic charged amphiphilic molecules such as alkyl sulfates, or alkyl-aryl-sulfates; non-ionic amphiphilic molecules such as alkyl polyglycosides or derivatives thereof, such as Plantacare® (available from Henkel KGaA), or alkyl alcohol poly alkylene ethers or derivatives thereof such as Laureth-9.

Preferred excipients are α-tocopherol, or derivatives of α-tocopherol such as α-tocopherol succinate. Other preferred tocopherol derivatives for use in the invention include D-α tocopherol, D-δ tocopherol, D-γ tocopherol and DL-α-tocopherol. Preferred derivatives of tocopherols that may be used include acetates, succinates, phosphoric acid esters, formiates, propionates, butyrates, sulfates and gluconates. Alpha-tocopherol succinate is particularly preferred. The α-tocopherol or derivative is present in an amount sufficient to stabilise the haemagglutinin.

Other suitable excipients may be identified by methods standard in the art, and tested for example using the SRD method for stability analysis as described herein.

In a preferred aspect the invention provides an influenza virus antigen preparation comprising at least one stable influenza B strain haemagglutinin antigen.

The invention provides in a further aspect a method for preparing a stable haemagglutinin antigen which method comprises purifying the antigen in the presence of a stabilising micelle modifying excipient, preferably α-tocopherol or a derivative thereof such as α-tocopherol succinate.

Further provided by the invention are vaccines comprising the antigen preparations described herein and their use in a method for prophylaxis of influenza infection or disease in a subject which method comprises administering to the subject a vaccine according to the invention.

The vaccine may be administered by any suitable delivery route, such as intradermal, mucosal e.g. intranasal, oral, intramuscular or subcutaneous. Other delivery routes are well known in the art.

Intradermal delivery is preferred. Any suitable device may be used for intradermal delivery, for example short needle devices such as those described in U.S. Pat. No. 4,886,499, U.S. Pat. No. 5,190,521, U.S. Pat. No. 5,328,483, U.S. Pat. No. 5,527,288, U.S. Pat. No. 4,270,537, U.S. Pat. No. 5,015,235, U.S. Pat. No. 5,141,496, U.S. Pat. No. 5,417,662. Intradermal vaccines may also be administered by devices which limit the effective penetration length of a needle into the skin, such as those described in WO99/34850 and EP1092444, incorporated herein by reference, and functional equivalents thereof. Also suitable are jet injection devices which deliver liquid vaccines to the dennis via a liquid jet injector or via a needle which pierces the stratum corneum and produces a jet which reaches the dermis. Jet injection devices are described for example in U.S. Pat. No. 5,430,381, U.S. Pat. No. 5,599,302, U.S. Pat. No. 5,334,144, U.S. Pat. No. 5,993,412. U.S. Pat. No. 5,649,912, U.S. Pat. No. 5,569,489, U.S. Pat. No. 5,704,911, U.S. Pat. No. 5,383,351, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537.

Also suitable are ballistic powder/particle delivery devices which use compressed gas to accelerate vaccine in powder form through the outer layers of the skin to the dermis. Additionally, conventional syringes may be used in the classical mantoux method of intradermal administration. However, the use of conventional syringes requires highly skilled operators and thus devices which are capable of accurate delivery without a highly skilled user are preferred.

The invention thus provides a method for the prophylaxis of influenza infection or disease in a subject which method comprises administering to the subject intradermally an influenza vaccine according to the invention.

The invention also extends to intradermal devices in combination with a vaccine according to the present invention, in particular with devices disclosed in WO99/34850 or EP1092444, for example.

Also provided is the use of a micelle modifying excipient, preferably α-tocopherol or a derivative thereof as a haemagglutinin stablilser in the manufacture of an influenza vaccine.

The invention applies particularly but not exclusively to the stabilisation of B strain influenza haemagglutinin.

Preferably the stabilised HA of the present invention is stable for 6 months, more preferably 12 months.

Preferably the α-tocopherol is in the form of an ester, more preferably the succinate or acetate and most preferably the succinate.

Preferred concentrations for the α-tocopherol or derivative are between 1 μg/ml-10 mg/ml, more preferably between 10 μg/ml-500 μg/ml.

The vaccine according to the invention generally contains both A and B strain virus antigens, typically in a trivalent composition of two A strains and one B strain. However, divalent and monovalent vaccines are not excluded. Monovalent vaccines may be advantageous in a pandemic situation, for example, where it is important to get as much vaccine produced and administered as quickly as possible.

The non-live flu antigen preparation for use in the invention may be selected from the group consisting of split virus antigen preparations, subunit antigens (either recombinantly expressed or prepared from whole virus), inactivated whole virus which may be chemically inactivated with e.g. formaldehyde, β-propiolactone or otherwise inactivated e.g. U.V. or heat inactivated. Preferably the antigen preparation is either a split virus preparation, or a subunit antigen prepared from whole virus, particularly by a splitting process followed by purification of the surface antigen. Most preferred are split virus preparations.

Preferably the concentration of haemagglutinin antigen for each strain of the influenza virus preparation is 1-1000 μg per ml, more preferably 3-300 μg per ml and most preferably about 30 μg per ml, as measured by a SRD assay.

The vaccine according to the invention may further comprise an adjuvant or immunostimulant such as but not limited to detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

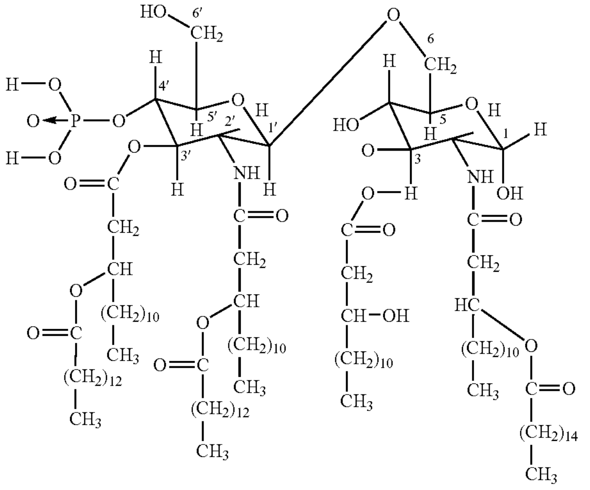

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A preferred form of 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, *Int.Arch.Allergy.Immunol.,* 79(4):392-6; Hilgers et al., 1987, Immunology, 60(1):141-6; and EP 0 549 074 B1). A particularly preferred bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja *Saponaria* Molina), and fractions thereof, are described in U.S. Pat. No. 5,057,540 and "Saponins as vaccine adjuvants", Kensil, C. R., *Crit Rev Ther Drug Carrier Syst,* 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as *Gypsophila* and *Saponaria* (Bomford et al., Vaccine, 10(9):572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21 and 3D-MPL in an oil in water emulsion is described in WO 95/17210 and is a preferred formulation.

Accordingly in one embodiment of the present invention there is provided a vaccine comprising an influenza antigen preparation of the present invention adjuvanted with detoxified lipid A or a non-toxic derivative of lipid A, more preferably adjuvanted with a monophosphoryl lipid A or derivative thereof.

Preferably the vaccine additionally comprises a saponin, more preferably QS21.

Preferably the formulation additionally comprises an oil in water emulsion. The present invention also provides a method for producing a vaccine formulation comprising mixing an antigen preparation of the present invention together with a pharmaceutically acceptable excipient, such as 3D-MPL.

The vaccines according to the invention may further comprise at least one surfactant which may be in particular a non-ionic surfactant. Suitable non-ionic surfactants are selected from the group consisting of the octyl- or nonylphenoxy polyoxyethanols (for example the commercially available Triton™ series), polyoxyethylene sorbitan esters (Tween™ series) and polyoxyethylene ethers or esters of general formula (I):

$$HO(CH_2CH_2O)_n\text{-}A\text{-}R \quad (I)$$

wherein n is 1-50, A is a bond or —C(O)—, R is $C_{1-50}$ alkyl or phenyl $C_{1-50}$ alkyl; and combinations of two or more of these.

Preferred surfactants falling within formula (I) are molecules in which n is 4-24, more preferably 6-12, and most preferably 9; the R component is $C_{1-50}$, preferably $C_4$-$C_{20}$ alkyl and most preferably $C_{12}$ alkyl.

Octylphenoxy polyoxyethanols and polyoxyethylene sorbitan esters are described in "Surfactant systems" Eds: Attwood and Florence (1983, Chapman and Hall). Octylphenoxy polyoxyethanols (the octoxynols), including t-octylphenoxypolyethoxyethanol (Triton X-100™) are also described in Merck Index Entry 6858 (Page 1162, $12^{th}$ Edition, Merck & Co. Inc., Whitehouse Station, N.J., USA; ISBN 0911910-12-3). The polyoxyethylene sorbitan esters, including polyoxyethylene sorbitan monooleate (Tween 80™) are described in Merck Index Entry 7742 (Page 1308, $12^{th}$ Edition, Merck & Co. Inc., Whitehouse Station, N.J., USA; ISBN 0911910-12-3). Both may be manufactured using methods described therein, or purchased from commercial sources such as Sigma Inc.

Particularly preferred non-ionic surfactants include Triton X-45, t-octylphenoxy polyethoxyethanol (Triton X-100), Triton X-102, Triton X-114, Triton X-165, Triton X-205, Triton X-305, Triton N-57, Triton N-101, Triton N-128, Breij 35, polyoxyethylene-9-lauryl ether (laureth 9) and polyoxyethylene-9-stearyl ether (steareth 9). Triton X-100 and laureth 9 are particularly preferred. Also particularly preferred is the polyoxyethylene sorbitan ester, polyoxyethylene sorbitan monooleate (Tween 80™).

Further suitable polyoxyethylene ethers of general formula (I) are selected from the following group: polyoxyethylene-8-stearyl ether, polyoxyethylene-4-lauryl ether, polyoxyethylene-35-lauryl ether, and polyoxyethylene-23-lauryl ether.

Alternative terms or narnes for polyoxyethylene lauryl ether are disclosed in the CAS registry. The CAS registry number of polyoxyethylene-9 lauryl ether is: 9002-92-0. Polyoxyethylene ethers such as polyoxyethylene lauryl ether are described in the Merck index ($12^{th}$ ed: entry 7717, Merck & Co. Inc., Whitehouse Station, N.J., USA; ISBN 0911910-12-3). Laureth 9 is formed by reacting ethylene oxide with dodecyl alcohol, and has an average of nine ethylene oxide units.

Two or more non-ionic surfactants from the different groups of surfactants described may be present in the vaccine formulation described herein. In particular, a combination of a polyoxyethylene sorbitan ester such as polyoxyethylene sorbitan monooleate (Tween 80™) and an octoxynol such as t-octylphenoxypolyethoxyethanol (Triton) X-100™ is preferred. Another particularly preferred combination of non-ionic surfactants comprises laureth 9 plus a polyoxyethylene sorbitan ester or an octoxynol or both.

Non-ionic surfactants such as those discussed above have preferred concentrations in the final vaccine composition as follows: polyoxyethylene sorbitan esters such as Tween 80™: 0.01 to 1%, most preferably about 0.1% (w/v); octyl- or nonylphenoxy polyoxyethanols such as Triton X-100™ or other detergents in the Triton series: 0.001 to 0.1%, most preferably 0.005 to 0.02% (w/v); polyoxyethylene ethers of general formula (I) such as laureth 9: 0.1 to 20%, preferably 0.1 to 10% and most preferably 0.1 to 1% or about 0.5% (w/v).

For certain vaccine formulations, other vaccine components may be included in the formulation. As such the formulations of the present invention may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particularly preferred example is sodium deoxycholate (NaDOC) which may be present in the final vaccine dose.

Also provided by the invention are pharmaceutical kits comprising a vaccine administration device filled with a vaccine according to the invention. Such administration devices include but are not limited to needle devices, liquid jet devices, powder devices, and spray devices (for intranasal use).

The influenza virus antigen preparations according to the invention may be derived from the conventional embryonated egg method, or they may be derived from any of the new generation methods using tissue culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells. Suitable cell substrates are not limited to cell lines; for example primary cells such as chicken embryo fibroblasts are also included.

The influenza virus antigen preparation may be produced by any of a number of commercially applicable processes, for example the split flu process described in patent no. DD 300 833 and DD 211 444, incorporated herein by reference. Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including Triton X-100 (for example in a process described in Lina et al, 2000, Biologicals 28, 95-103) and Triton N-101, or combinations of any two or more detergents.

The preparation process for a split vaccine will include a number of different filtration and/or other separation steps such as ultracentrifugation, ultrafiltration, zonal centrifugation and chromatography (e.g ion exchange) steps in a variety of combinations, and optionally an inactivation step, e.g., with heat, formaldehyde or β-propiolactone or U.V. which may be carried out before or after splitting. The splitting process may be carried our as a batch, continuous or semi-continuous process.

Preferred split flu vaccine antigen preparations according to the invention comprise a residual amount of Tween 80 and/or Triton X-100 remaining from the production process, although these may be added or their concentrations adjusted after preparation of the split antigen. Preferably both Tween 80 and Triton X-100 are present. The preferred ranges for the final concentrations of these non-ionic surfactants in the vaccine dose are:

Tween 80: 0.01 to 1%, more preferably about 0.1% (v/v)

Triton X-100: 0.001 to 0.1 (% w/v), more preferably 0.005 to 0.02% (w/v).

Alternatively the influenza virus antigen preparations according to the invention may be derived from a source other than the live influenza virus, for example the haemagglutinin antigen may be produced recombinantly.

The invention will now be further described in the following, non-limiting examples.

EXAMPLES

Example 1

Preparation of Influenza Virus Antigen Preparation Using α-tocopherol Succinate as a Stabiliser for a Preservative-free Vaccine (Thiomersal-reduced Vaccine)

Monovalent split vaccine was prepared according to the following procedure.

Preparation of Virus Inoculum

On the day of inoculation of embryonated eggs a fresh inoculum is prepared by mixing the working seed lot with a phosphate buffered saline containing gentamycin sulphate at 0.5 mg/ml and hydrocortisone at 25 μg/ml. (virus strain-dependent). The virus inoculum is kept at 2-8° C.

Inoculation of Embryonated Eggs

Nine to eleven day old embryonated eggs are used for virus replication. Shells are decontaminated. The eggs are inoculated with 0.2 ml of the virus inoculum. The inoculated eggs are incubated at the appropriate temperature (virus strain-dependent) for 48 to 96 hours. At the end of the incubation period, the embryos are killed by cooling and the eggs are stored for 12-60 hours at 2-8° C.

Harvest

The allantoic fluid from the chilled embryonated eggs is harvested. Usually, 8 to 10 ml of crude allantoic fluid is collected per egg.

Concentration and Purification of Whole Virus From Allantoic Fluid

1. Clarification

The harvested allantoic fluid is clarified by moderate speed centrifugation (range: 4000-14000 g).

2. Adsorption Step

To obtain a $CaHPO_4$ gel in the clarified virus pool, 0.5 mol/L $Na_2HPO_4$ and 0.5 mol/L $CaCl_2$ solutions are added to reach a final concentration of $CaHPO_4$ of 1.5 g to 3.5 g $CaHPO_4$/liter depending on the virus strain.

After sedimentation for at last 8 hours, the supernatant is removed and the sediment containing the influenza virus is resolubilised by addition of a 0.26 mol/L EDTA-$Na_2$ solution, dependent on the amount of $CaHPO_4$ used.

3. Filtration

The resuspended sediment is filtered on a 6 μm filter membrane.

4. Sucrose Gradient Centrifugation

The influenza virus is concentrated by isopycnic centrifugation in a linear sucrose gradient (0.55% (w/v)) containing 100 μg/ml Thiomersal. The flow rate is 8-15 liters/hour.

At the end of the centrifugation, the content of the rotor is recovered by four different fractions (the sucrose is measured in a refractometer):

| | |
|---|---|
| fraction 1 | 55–52% sucrose |
| fraction 2 | approximately 52–38% sucrose |
| fraction 3 | 38–20% sucrose* |
| fraction 4 | 20–0% sucrose |

*virus strain-dependent: fraction 3 can be reduced to 15% sucrose.

For further vaccine preparation, only fractions 2 and 3 are used.

Fraction 3 is washed by diafiltration with phosphate buffer in order to reduce the sucrose content to approximately below 6%. The influenza virus present in this diluted fraction is pelleted to remove soluble contaminants.

The pellet is resuspended and thoroughly mixed to obtain a homogeneous suspension. Fraction 2 and the resuspended pellet of fraction 3 are pooled and phosphate buffer is added to obtain a volume of approximately 40 liters. This product is the monovalent whole virus concentrate.

5. Sucrose Gradient Centrifugation with Sodium Deoxycholate

The monovalent whole influenza virus concentrate is applied to a ENI-Mark II ultracentrifuge. The K3 rotor contains a linear sucrose gradient (0.55% (w/v)) where a sodium deoxycholate gradient is additionally overlayed. Tween 80 is present during splitting up to 0.1% (w/v) and Tocopherol succinate is added for B-strain-viruses up to 0.5 mM. The maximal sodium deoxycholate concentration is 0.7-1.5% (w/v) and is strain dependent. The flow rate is 8-15 liters/hour.

At the end of the centrifugation, the content of the rotor is recovered by three different fractions (the sucrose is measured in a refractometer) Fraction 2 is used for further processing. Sucrose content for fraction limits (47-18%) varies according to strains and is fixed after evaluation:

6. Sterile Filtration

The split virus fraction is filtered on filter membranes ending with a 0.2 μm membrane. Phosphate buffer containing 0.025% (w/v) Tween 80 and (for B strain viruses) 0.5 mM Tocopherol succinate is used for dilution. The final volume of the filtered fraction 2 is 5 times the original fraction volume.

7. Inactivation

The filtered monovalent material is incubated at 22±2° C. for at most 84 hours (dependent on the virus strains, this incubation can be shortened). Phosphate buffer containing 0.025% (w/v). Tween 80 is then added in order to reduce the total protein content down to max. 250 μg/ml. For B strain viruses, a phosphate buffered saline containing 0.025% (w/v) Tween 80 and 0.25 mM Tocopherol succinate is applied for dilution to reduce the total protein content down to 250 μg/ml. Formaldehyde is added to a final concentration of 50 μg/ml and the inactivation takes place at 20° C.±2° C. for at least 72 hours.

8. Ultrafiltration

The inactivated split virus material is concentrated at least 2 fold in a ultrafiltration unit, equipped with cellulose acetate membranes with 20 kDa MWCO. The Material is subsequently washed with phosphate buffer containing 0.025% (w/v) Tween 80 and following with phosphate buffered saline containing 0.01% (w/v) Tween. For B strain virus a phosphate buffered saline containing 0.01% (w/v) Tween 80 and 0.1 mM Tocopherol succinate is used for washing.

9. Final Sterile Filtration

The material after ultrafiltration is filtered on filter membranes ending with a 0.2 μm membrane. Filter membranes are rinsed and the material is diluted if necessary such that the protein concentration does not exceed 500 μg/ml with phosphate buffered saline containing 0.01% (w/v) Tween 80 and (for B strain viruses) 0.1 mM Tocopherol succinate.

10. Storage

The monovalent final bulk is stored at 2-8° C. for a maximum of 18 months.

Stability

TABLE 1

Comparison of time dependent HA content (μg/ml) measured by SRD in monovalent final bulks.

| Strain | Stabiliser | After production | 4 weeks at 30° C. | 6 month at 2–8° C. | 12 month at 2–8° C. |
|---|---|---|---|---|---|
| B/Yamanashi/166/98 | Tocopherylsuccinate (residual mercury 3 μg/ml) | 169 | 139 (82%) | 172 (>100%) | ND |
| B/Yamanashi/166/98 | Thiomersal (108 μg/ml) | 192 | 160 (83%) | 186 (97%) | 178 (93%) |
| B/Yamanashi/166/98 | None (residual mercury 3 μg/ml) | 191 | 122 (60%) | 175 (92%) | 154 (81%) |
| B/Johannesburg/5/99 | Tocopherylsuccinate (residual mercury 4 μg/ml) | 166 | 183 (>100%) | 158 (95%) | 179 (>100%) |
| B/Johannesburg/5/99 | Tocopherylsuccinate (residual mercury 4 μg/ml) | 167 | 179 (>100%) | 158 (95%) | 178 (>100%) |
| B/Johannesburg/5/99 | Tocopherylsuccinate (residual mercury 3 μg/ml) | 144 | 151 (>100%) | 130 (90%) | 145 (>100%) |

TABLE 1-continued

Comparison of time dependent HA content (μg/ml) measured by SRD in monovalent final bulks.

| Strain | Stabiliser | After production | 4 weeks at 30° C. | 6 month at 2–8° C. | 12 month at 2–8° C. |
|---|---|---|---|---|---|
| B/Johannesburg/5/99* | Thiomersal | 159 | ND | 172 (>100%) | 154 (97%) |
| B/Johannesburg/5/99** | None | 169 | 107 (63%) | 153 (90%) | ON |

*produced according to licensed FLUARIX ™,
**produced according to example 1 without Tocopherylsuccinate, ON: Ongoing, ND not determined

Example 2

Preparation of Influenza Vaccine Using α-tocopherol Succinate as a Stabiliser for a Thiomersal-reduced Vaccine Monovalent final bulks of three strains, A/New Caldonia/20/99 (H1N1) IVR-116, A/Panama/2007/99 (H3N2) Resvir-17 and B/Yamanashi/166/98 were produced according to the method described in Example 1.

Pooling

The appropriate amount of monovalent final bulks was pooled to a final HA-concentration of 30 μg/ml for A/New Caldonia/20/99 (H1N1) IVR-116, A/Panama/2007/99 (H3N2) Resvir-17, respectively and of 39 μg/ml for B/Yamanashi/166/98. Tween 80 and Triton X-100 were adjusted to 580 μg/ml and 90 μg/ml, respectively. The final volume was adjusted to 3 l with phosphate buffered saline. The trivalent pool was filtered ending with 0.8 μm cellulose acetate membrane to obtain the trivalent final bulk. Trivalent final bulk was filled into syringes at least 0.5 mL in each.

wells (3 mm Ø) are punched into the agarose. 10 microliters of appropriate dilutions of the reference and the sample are loaded in the wells. The plates are incubated for 24 hours at room temperature (20 to 25° C.) in a moist chamber. After that, the plates are soaked overnight with NaCl-solution and washed briefly in distilled water. The gel is then pressed and dried. When completely dry, the plates are stained on Coomassie Brillant Blue solution for 10 min and destained twice in a mixture of methanol and acetic acid until clearly defined stained zones become visible. After drying the plates, the diameter of the stained zones surrounding antigen wells is measured in two directions at right angles. Alternatively equipment to measure the surface can be used. Dose-response curves of antigen dilutions against the surface are constructed and the results are calculated according to standard slope-ratio assay methods (Finney, D. J. (1952). Statistical Methods in Biological Assay. London: Griffin, Quoted in: Wood, J M, et al (1977). J. Biol. Standard. 5, 237-247).

TABLE 2

Comparison of time dependent HA content measured by SRD in trivalent final bulks which was recovered from syringes.

| Vaccine formul. | Strain | 0 months | 2 months | 4 months | 6 months |
|---|---|---|---|---|---|
| Influenza vaccine without stabilizer | A/NCal/20/99 | 33 (32–34) | 32 (31–33) | 36 (34–38) | 31 (30–32) |
| | A/Pan/2007/99 | 29 (27–31) | 31 (28–34) | 34 (32–36) | 32 (31–33) |
| | B/Yam/166/98 | 36 (34–38) | 33 (32–34) | 32 (30–34) | 31 (29–33) |
| Influenza vaccine containing | A/NCal/20/99 | 31 (30–32) | 32 (31–33) | 36 (34–38) | 32 (31–33) |
| alpha-tocopherol succinate | A/Pan/2007/99 | 33 (30–36) | 33 (30–36) | 36 (35–37) | 33 (31–35) |
| | B/Yam/166/98 | 37 (35–39) | 36 (34–38) | 38 (35–41) | 36 (33–39) |

Example 3

SRD Method Used to Measure Haemagglutinin Content

Glass plates (12.4-10.0 cm) are coated with an agarose gel containing a concentration of anti-influenza HA serum that is recommended by NIBSC. After the gel has set, 72 sample

Example 4

Clinical Testing of α-tocopherol Stabilised Influenza Vaccine (Reduced Thiomersal)

Syringes obtained as described in Example 2 are used for clinical testing

H3N2: A/Panama/2007/99 RESVIR-17

H1N1: A/New Caledonia/20/99 (H1N1) IVR-116

B: B/Yamanashi/166/98

TABLE 3

| | Adults 18–60 years | thio-reduced H3N2 | H1N1 | B | thio-plus H3N2 | H1N1 | B |
|---|---|---|---|---|---|---|---|
| pre-vacc. | GMT | 47 | 41 | 111 | 55 | 37 | 102 |
| | Titer <10 [%] | 10.3% | 13.8% | 1.7% | 5.3% | 12.3% | 8.8% |
| | Titer ≧40, SPR [%] | 60.3% | 55.2% | 75.9% | 70.2% | 52.6% | 75.4% |
| post-vacc. | Seroconv. rate [%] | 10.3% | 13.8% | 1.7% | 5.3% | 12.3% | 8.8% |
| | Significant Increase in antibody titer [%] | 58.6% | 74.1% | 58.6% | 63.2% | 73.7% | 52.6% |
| | Seroconversions [%] | 58.6% | 74.1% | 58.6% | 63.2% | 73.7% | 52.6% |
| | GMT | 328 | 525 | 766 | 324 | 359 | 588 |
| | Fold GMT | 7.3 | 13.0 | 6.9 | 5.9 | 9.8 | 5.9 |
| | Titer ≧40, SPR [%] | 100.0% | 100.0% | 100.0% | 100.0% | 100.0% | 100.0% |

n.d. = C.I. for proportion p = n/N is not defined, because p *(1-p)*N < 9
n/N = responders (n) as part of number of subjects of the (sub)population (N), i.e. seroconversions or significant increase, see also: CPMAP/BWP/214/96 Mar. 12, 1997, p.17ff
GMT = geometric mean titer, reciprocal
95% C.I. = 95% confidence interval,
SPR = Seroprotection rate: proportion of subjects with a protective titer pre- or postvaccination ≧40
titer = HI-antibody titer
Seroconversion rate = proportion of subjects with antibody increase from <10 prevaccination to ≧40 postvaccination
fold GMT = fold increase of GMT
Significant increase = proportion of subjects with an antibody titer ≧10 prevaccination and 4-fold antibody increase postvaccination (two steps of titer)
req. = EU requirement
Seroconversions = neg to pos or g.e. 4-fold (neg: titer <10, pos: titer ≧40) = proportion of subjects with either seroconversion (<10 to ≧40) or significant increase.
Results show that the vaccine is able to offer equivalent protection to vaccines containing thiomersal as a preservative.

Example 5a

Preparation Influenza Virus Antigen Preparation Using α-tocopherol Succinate as a Stabiliser for a Thiomersal-free Vaccine Monovalent split vaccine was prepared according to the following procedure.

Preparation of Virus Inoculum

On the day of inoculation of embryonated eggs a fresh inoculum is prepared by mixing the working seed lot with a phosphate buffered saline containing gentamycin sulphate at 0.5 mg/ml and hydrocortisone at 25 μg/ml. (virus strain-dependent). The virus inoculum is kept at 2-8° C.

Inoculation of Embryonated Eggs

Nine to eleven day old embryonated eggs are used for virus replication. Shells are decontaminated. The eggs are inoculated with 0.2 ml of the virus inoculum. 60,000 inoculated eggs are incubated at the appropriate temperature (virus strain-dependent) for 48 to 96 hours. At the end of the incubation period, the embryos are killed by cooling and the eggs are stored for 12-60 hours at 2-8° C.

Harvest

The allantoic fluid from the chilled embryonated eggs is harvested. Usually, 8 to 10 ml of crude allantoic fluid is collected per egg.

Concentration and Purification of Whole Virus from Allantoic Fluid

Clarification

The harvested allantoic fluid is clarified by moderate speed centrifugation (range: 4000-14000 g).

Precipitation Step

Saturated ammonium sulfate solution is added to the clarified virus pool to reach a final ammonium sulfate concentration of 0.5 mol/L. After sedimentation for at least 1 hour, the precipitate is removed by filtration on depth filters (typically 0.5 μm)

Filtration

The clarified crude whole virus bulk is filtered on filter membranes ending with a validated sterile membrane (typically 0.2 μm).

Ultrafiltration

The sterile filtered crude monovalent whole virus bulk is concentrated on a cassettes equipped with 1000 kDa MWCO BIOMAX™ membrane at least 6 fold. The concentrated retentate is washed with phosphate buffered saline at least 1.8 times.

Sucrose Gradient Centrifugation

The influenza virus is concentrated by isopycnic centrifugation in a linear sucrose gradient (0.55% (w/v)). The flow rate is 8-15 liters/hour.

At the end of the centrifugation, the content of the rotor is recovered by four different fractions (the sucrose is measured in a refractometer):

| | |
|---|---|
| fraction 1 | 55–52% sucrose |
| fraction 2 | approximately 52–38% sucrose |
| fraction 3 | 38–20% sucrose* |
| fraction 4 | 20–0% sucrose |

*virus strain-dependent: fraction 3 can be reduced to 15% sucrose.

For further vaccine preparation, either only fraction 2 is used or fraction 2 together with a further purified fraction 3 are used.

Fraction 3 is washed by diafiltration with phosphate buffer in order to reduce the sucrose content to approximately below 6%. Optionally this step may be omitted. The influenza virus present in this diluted fraction is pelleted to remove soluble contaminants.

The pellet is resuspended and thoroughly mixed to obtain a homogeneous suspension. Fraction 2 and the resuspended pellet of fraction 3 are pooled and phosphate buffer is added to obtain a volume of approximately 40 liters. This product is the monovalent whole virus concentrate.

Sucrose Gradient Centrifugation with Sodium Deoxycholate

The monovalent whole influenza virus concentrate is applied to a ENI-Mark II ultracentrifuge. The K3 rotor contains a linear sucrose gradient (0.55% (w/v)) where a sodium deoxycholate gradient is additionally overlayed. Tween 80 is present during splitting up to 0.1% (w/v) and Tocopherylsuccinate is added for B-strain viruses up to 0.5 mM. The maximal sodium deoxycholate concentration is 0.7-1.5% (w/v) and is strain dependent. The flow rate is 8-15 liters/hour.

At the end of the centrifugation, the content of the rotor is recovered by three different fractions (the sucrose is measured in a refractometer) Fraction 2 is used for further processing. Sucrose content for fraction limits (47-18%) varies according to strains and is fixed after evaluation:

Sterile Filtration

The split virus fraction is filtered on filter membranes ending with a 0.2 μm membrane. Phosphate buffer containing 0.025% (w/v) Tween 80 and (for B strains) 0.5 mM Tocopherylsuccinate is used for dilution. The final volume of the filtered fraction 2 is 5 times the original fraction volume.

Inactivation

The filtered monovalent material is incubated at 22±2° C. for at most 84 hours (dependent on the virus strains, this incubation can be shortened). Phosphate buffer containing 0.025% (w/v) Tween 80 is then added in order to reduce the total protein content down to max. 450 μg/ml. For B-strains a phosphate buffered saline containing 0.025% (w/v) Tween 80 and 0.25 mM Tocopherylsuccinate is applied for dilution to reduce the total protein content down to 450 μg/ml. Formaldehyde is added to a final concentration of 100 μg/ml and the inactivation takes place at 20° C. ±2° C. for at least 72 hours.

Ultrafiltration

The inactivated split virus material is concentrated at least 2 fold in a ultrafiltration unit, equipped with cellulose acetate membranes with 20 kDa MWCO. The Material is subsequently washed with phosphate buffer containing 0.025% (w/v) Tween 80 and following with phosphate buffered saline containing 0.01% (w/v) Tween. For B-strain viruses a phosphate buffered saline containing 0.01% (w/v) Tween 80 and 0.1 mM Tocopherylsuccinate is used for washing.

Final Sterile Filtration

The material after ultrafiltration is filtered on filter membranes ending with a 0.2 μm membrane. Filter membranes are rinsed and the material is diluted if necessary that the protein concentration does not exceed 500 μg/ml with phosphate buffered saline containing 0.01% (w/v) Tween 80 and, specific for B strains, 0.1 mM Tocopherylsuccinate.

Storage

The monovalent final bulk is stored at 2-8° C. for a maximum of 18 months.

Stability

TABLE 4

Comparison of time dependent HA content (μg/ml) measured by SRD in monovalent final bulks.

| Strain | Stabiliser | After production | 4 weeks at 30° C. | 6 month at 2–8° C. |
|---|---|---|---|---|
| B/Johannesburg/5/99 | Tocopherol succinate | 214 | 196 (92%) | 206 (96%) |
| B/Johannesburg/5/99** | None | 169 | 107 (63%) | 153 (90%) |

**produced according to example 1 without Tocopherylsuccinate.

Example 5b

Preparation of Influenza Virus Antigen Preparation Using α-tocopherol Succinate as a Stabiliser for a Thiomersal-free Vaccine A preferred variation of the method described in Example 5a is as follows:

Harvesting of the whole virus is followed by the precipitation step (ammonium sulfate precipitation). This is followed by the clarification step where the fluid is clarified by moderate speed centrifugation (range 4000-14000 g). Thus the order of the precipitation and clarification steps is reversed compared to Example 5a.

Sterile filtration, ultrafiltration and ultracentrifugation (sucrose gradient centrifugation) steps follow as for Example 5a. However, there is no need for reprocessing step of the fractions resulting from the ultracentrifugation step.

The remaining steps in the process are as described in Example 5a.

Thus, the summarised process in this example is as follows:

Harvest
Precipitation (ammonium sulfate)
Clarification
Sterile filtration
Ultrafiltration
Ultracentrifugation
Splitting (preferably sodium deoxycholate)
Sterile filtration
Inactivation
Ultrafiltration
Final sterile filtration Another preferred variation of Example 5a involves a prefiltration step before the first sterile filtration. This uses a membrane which does not sterile filter but which enables the removal of contaminants e.g. albumin prior to sterile filtration. This can result in a better yield. A suitable membrane for prefiltration is about 0.8 μm to about 1.8 μm, for example 1.2 μm. The prefiltration step can be used in the scheme of Example 5a or Example 5b.

Example 6

Preparation of Influenza Vaccine Using α-tocopherol Succinate as a Stabiliser for a Thiomersal-free Vaccine Monovalent final bulks of three strains, A/New Caldonia/20/99 (H1N1) IVR-116, A/Panama/2007/99 (H3N2) Resvir-17 and B/Yamanashi/166/98 were produced according to the method described in Example 5.

Pooling

The appropriate amount of monovalent final bulks were pooled to a final HA-concentration of 30 μg/ml for A/New Caldonia/20/99 (H1N1) IVR-116, A/Panama/2007/99 (H3N2) Resvir-17, respectively and of 36 μg/ml for B/Johannesburg/5/97. Tween 80 and Triton X-100 were adjusted to 580 μg/ml and 90 μg/ml, respectively. The final volume was adjusted to 3 l with phosphate buffered saline. The trivalent pool was filtered ending with 0.8 μm cellulose acetate membrane to obtain the trivalent final bulk. Trivalent final bulk was filled into syringes at least 0.5 mL in each.

TABLE 5

Comparison of time dependent HA content (μg/ml) measured by SRD in trivalent final bulks.

| Vaccine formul. | Strain | 0 months | 4 weeks at 30° C. | 6 months at 2-8° C. |
|---|---|---|---|---|
| Influenza vaccine without stabilizer | A/NCal/20/99 | 31 | 32 | 30 |
| | A/Pan/2007/99 | 31 | 34 | 33 |
| | B/Joh/5/99* | 35 | 25 | 31 |
| Influenza vaccine containing alpha-tocopherol succinate | A/NCal/20/99 | 34 | 35 | 34 |
| | A/Pan/2007/99 | 33 | 33 | 34 |
| | B/Joh/5/99** | 29 | 25 | 28 |

*Formulation was based on target concentration of 39 μg/ml.
**Formulation was based on target concentration of 34 μg/ml.

Example 7

Preparation of Influenza Virus Antigen Preparation Using Sodium Lauryl Sulfate as a Stabiliser for a Preservative-free Vaccine (Thiomersal-reduced Vaccine)

Monovalent Whole Virus Concentrate of B/Johannesburg/5/99 was Obtained as Described in Example 1.

Sucrose Gradient Centrifugation with Sodium Deoxycholate

The monovalent whole influenza virus concentrate is applied to a ENI-Mark II ultracentrifuge. The K3 rotor contains a linear sucrose gradient (0.55% (w/v)) where a sodium deoxycholate gradient is additionally overlayed. Tween 80 is present during splitting up to 0.1% (w/v). The maximal sodium deoxycholate concentration is 0.7-1.5% (w/v) and is strain dependent. The flow rate is 8-15 liters/hour.

At the end of the centrifugation, the content of the rotor is recovered by three different fractions (the sucrose is measured in a refractometer) Fraction 2 is used for further processing. Sucrose content for fraction limits (47-18%) varies according to strains and is fixed after evaluation:

Sterile Filtration

A sample of fraction 2 of 10 ml was taken for further processing. The split virus fraction is filtered on filter membranes ending with a 0.2 μm membrane. Phosphate buffer containing 0.025% (w/v) Tween 80 and 0.5 mM sodium lauryl sulfate is used for dilution. The final volume of the filtered fraction 2 is 5 times the original fraction volume.

Inactivation

The filtered monovalent material is incubated at 22±2° C. for at most 84 hours (dependent on the virus strains, this incubation can be shortened). Phosphate buffered saline containing 0.025% (w/v) Tween 80 and 0.5 mM sodium laurylsulfate is then added in order to reduce the total protein content down to max. 250 μg/ml. Formaldehyde is added to a final concentration of 50 μg/ml and the inactivation takes place at 20° C.±2° C. for at least 72 hours.

Ultrafiltration

The inactivated split virus material is concentrated at least 2 fold in a ultrafiltration unit, equipped with cellulose acetate membranes with 20 kDa MWCO. The Material is subsequently washed with 4 volumes phosphate buffered saline containing 0.01% (w/v) Tween and 0.5 mM sodium lauryl sulfate.

Final Sterile Filtration

The material after ultrafiltration is filtered on filter membranes ending with a 0.2 μM membrane. Filter membranes are rinsed and the material is diluted if necessary that the protein concentration does not exceed 500 μg/ml with phosphate buffered saline containing 0.01% (w/v) Tween 80 and 0.5 mM sodium lauryl sulfate.

Storage

The monovalent final bulk is stored at 2-8° C.

TABLE 7

Comparison of time dependent HA content measured by SRD in monovalent final bulks.

| | stabiliser | After production | 4 weeks at 30° C. |
|---|---|---|---|
| B/Johannesburg/5/99 | None* | 182 | 139 (77%) |
| B/Johannesburg/5/99 | Sodium lauryl sulfate | 288 | 264 (92%) |

*produced according to Example 7 without addition of sodium lauryl sulfate

Example 8

Preparation of Influenza Virus Antigen Preparation Using Plantacare or Laureth-9 as a Stabiliser for a Preservative-free Vaccine (Thiomersal-reduced Vaccine)

Monovalent Whole Virus Concentrate of B/Yamanashi/166/98 was Obtained as Described in Example 1.

Fragmentation

The monovalent whole influenza virus concentrate is diluted to a protein concentration of 1,000 μg/ml with phosphate buffered saline pH 7.4. Either Plantacare® 2000 UP or Laureth-9 is added to a final concentration of 1% (w/v). The material is slightly mixed for 30 min. Then the material is overlayed on a sucrose cushion 15% (w/w) in a bucket. Ultracentrifugation in a Beckman swing out rotor SW 28 is performed for 2 h at 25,000 rpm and 20° C.

Sterile Filtration

A supernatant was taken for further processing. The split virus fraction is filtered on filter membranes ending with a 0.2 μm membrane.

Inactivation

Phosphate buffered saline is added if necessary in order to reduce the total protein content down to max. 500 μg/ml. Formaldehyde is added to a final concentration of 100 μg/ml and the inactivation takes place at 20° C.±2° C. for at least 6 days.

Ultrafiltration

Tween 80 and Triton X 100 is adjusted in the inactivated material to 0.15% and 0.02% respectively. The inactivated split virus material is concentrated at least 2 fold in a ultrafiltration unit, equipped with cellulose acetate membranes with 30 kDa MWCO. The Material is subsequently washed with 4 volumes phosphate buffered saline.

Final Sterile Filtration

The material after ultrafiltration is filtered on filter membranes ending with a 0.2 μm membrane. Filter membranes are rinsed and the material is diluted that the protein concentration does not exceed 500 μg/ml with phosphate buffered saline Storage The monovalent final bulk is stored at 2-8° C.

TABLE 8

Comparison of time dependent HA content measured by SRD in monovalent final bulks.

| | stabiliser | After production | 4 weeks at 30° C. |
|---|---|---|---|
| B/Yamanashi/166/98 | None | 143 | 98 (68%) |
| B/Yamanashi/166/98 | Plantacare ® 2000 UP | 476 | 477 (100%) |
| B/Yamanashi/166/98 | Laureth-9 | 468 | 494 (>100%) |

Example 9

Clinical Testing of α-tocopherol Stabilised Influenza Vaccine (Reduced Thiomersal) in the Elderly Via ID and IM Administration A Preparation of Influenza Virus Antigen Preparation Monovalent split vaccine was prepared according to the following procedure.

Preparation of Virus Inoculum

On the day of inoculation of embryonated eggs a fresh inoculum is prepared by mixing the working seed lot with a phosphate buffered saline containing gentamycin sulphate at 0.5 mg/ml and hydrocortisone at 25 μg/ml. (virus strain-dependent). The virus inoculum is kept at 2-8° C.

Inoculation of Embryonated Eggs

Nine to eleven day old embryonated eggs are used for virus replication. Shells are decontaminated. The eggs are inoculated with 0.2 ml of the virus inoculum. The inoculated eggs are incubated at the appropriate temperature (virus strain-dependent) for 48 to 96 hours. At the end of the incubation period, the embryos are killed by cooling and the eggs are stored for 12-60 hours at 2-8° C.

Harvest

The allantoic fluid from the chilled embryonated eggs is harvested. Usually, 8 to 10 ml of crude allantoic fluid is collected per egg.

Concentration and Purification of Whole Virus From Allantoic Fluid

1. Clarification

The harvested allantoic fluid is clarified by moderate speed centrifugation (range: 4000-14000 g).

2. Adsorption Step

To obtain a $CaHPO_4$ gel in the clarified virus pool, 0.5 mol/L $Na_2HPO_4$ and 0.5 mol/L $CaCl_2$ solutions are added to reach a final concentration of $CaHPO_4$ of 1.5 g to 3.5 g $CaHPO_4$/liter depending on the virus strain.

After sedimentation for at last 8 hours, the supernatant is removed and the sediment containing the influenza virus is resolubilised by addition of a 0.26 mol/L EDTA-$Na_2$ solution, dependent on the amount of $CaHPO_4$ used.

3. Filtration

The resuspended sediment is filtered on a 6 μm filter membrane.

4. Sucrose Gradient Centrifugation

The influenza virus is concentrated by isopycnic centrifugation in a linear sucrose gradient (0.55% (w/v)) containing 100 μg/ml Thiomersal. The flow rate is 8-15 liters/hour.

At the end of the centrifugation, the content of the rotor is recovered by four different fractions (the sucrose is measured in a refractometer):

| | |
|---|---|
| fraction 1 | 55–52% sucrose |
| fraction 2 | approximately 52–38% sucrose |
| fraction 3 | 38–20% sucrose* |
| fraction 4 | 20–0% sucrose |

*virus strain-dependent: fraction 3 can be reduced to 15% sucrose.

For further vaccine preparation, only fractions 2 and 3 are used.

Fraction 3 is washed by diafiltration with phosphate buffer in order to reduce the sucrose content to approximately below 6%. The influenza virus present in this diluted fraction is pelleted to remove soluble contaminants.

The pellet is resuspended and thoroughly mixed to obtain a homogeneous suspension. Fraction 2 and the resuspended pellet of fraction 3 are pooled and phosphate buffer is added to obtain a volume of approximately 40 liters, a volume appropriate for 120,000 eggs/batch. This product is the monovalent whole virus concentrate.

5. Sucrose Gradient Centrifugation with Sodium Deoxycholate

The monovalent whole influenza virus concentrate is applied to a ENI-Mark II ultracentrifuge. The K3 rotor contains a linear sucrose gradient (0.55% (w/v)) where a sodium deoxycholate gradient is additionally overlayed. Tween 80 is present during splitting up to 0.1% (w/v) and Tocopherol succinate is added for B-strain-viruses up to 0.5 mM. The maximal sodium deoxycholate concentration is 0.7-1.5% (w/v) and is strain dependent. The flow rate is 8-15 liters/hour.

At the end of the centrifugation, the content of the rotor is recovered by three different fractions (the sucrose is measured in a refractometer) Fraction 2 is used for further processing. Sucrose content for fraction limits (47-18%) varies according to strains and is fixed after evaluation:

6. Sterile Filtration

The split virus fraction is filtered on filter membranes ending with a 0.2 μm membrane. Phosphate buffer containing 0.025% (w/v) Tween 80 and (for B strain viruses) 0.5 mM Tocopherol succinate is used for dilution. The final volume of the filtered fraction 2 is 5 times the original fraction volume.

7. Inactivation

The filtered monovalent material is incubated at 22±2° C. for at most 84 hours (dependent on the virus strains, this incubation can be shortened). Phosphate buffer containing 0.025% (w/v). Tween 80 is then added in order to reduce the total protein content down to max. 250 μg/ml. For B strain viruses, a phosphate buffered saline containing 0.025% (w/v) Tween 80 and 0.25 mM Tocopherol succinate is applied for dilution to reduce the total protein content down to 250 μg/ml. Formaldehyde is added to a final concentration of 50 μg/ml and the inactivation takes place at 20° C.±2° C. for at least 72 hours.

8. Ultrafiltration

The inactivated split virus material is concentrated at least 2 fold in a ultrafiltration unit, equipped with cellulose acetate membranes with 20 kDa MWCO. The Material is subsequently washed with phosphate buffer containing 0.025% (w/v) Tween 80 and following with phosphate buffered saline containing 0.01% (w/v) Tween. For B strain virus a phosphate buffered saline containing 0.01% (w/v) Tween 80 and 0.1 mM Tocopherol succinate is used for washing.

9. Final Sterile Filtration

The material after ultrafiltration is filtered on filter membranes ending with a 0.2 μm membrane. Filter membranes are rinsed and the material is diluted if necessary such that the protein concentration does not exceed 1,000 μg/ml but haemagglutinin concentration exceeds 180 μg/ml with phosphate buffered saline containing 0.01% (w/v) Tween 80 and (for B strain viruses) 0.1 mM Tocopherol succinate.

10. Storage

The monovalent final bulk is stored at 2-8° C. for a maximum of 18 months.

B Preparation of Influenza Vaccine

Monovalent final bulks of three strains, A/New Caldonia/20/99 (H1N1) IVR-116, A/Panama/2007/99 (H3N2) Resvir-17 and B/Johannesburg/5/99 were produced according to the method described in part A above.

Pooling

The appropriate amount of monovalent final bulks were pooled to a final HA-concentration of 60 μg/ml for A/New Caldonia/20/99 (H1N1) IVR-116, A/Panama/2007/99 (H3N2) Resvir-17, respectively and of 68 μg/ml for B/Johannesburg/5/99. Tween 80, Triton X-100 and Tocopherol succinate were adjusted to 1,000 μg/ml, 110 μg/ml and 160 μg/ml, respectively. The final volume was adjusted to 3 l with phosphate buffered saline. The trivalent pool was filtered ending with 0.8 μm cellulose acetate membrane to obtain the trivalent final bulk. Trivalent final bulk was filled into syringes at least 0.165 mL in each.

Vaccine Administration

The vaccine was supplied in pre-filled syringes and was administered intradermally in the deltoid region. The intradermal (ID) needle was as described in EP1092444, having a skin penetration limiter to ensure proper intradermal injection. Since formation of a wheal (papule) at the injection site demonstrates the good quality of ID administration, the investigator with the subject measured the exact size of the wheal 30 minutes after vaccination.

One dose (100 μl) contained the following components:

| HEMAGGLUTININ FROM THREE INFLUENZA STRAINS | |
|---|---|
| A/NEW CALEDONIA/20/99 | 6.0 μg |
| A/PANAMA/2007/99 | 6.0 μg |
| B/JOHANNESBURG 5/99 | 6.0 μg |
| THIOMERSAL PRESERVATIVE | 0.4 μg–0.8 μg |

B The above vaccine was compared a standard trivalent split influenza vaccine:

Fluarix™. The Fluarix vaccine was supplied in pre-filled syringes and was administered intramuscularly in the deltoid muscle. A needle of at least 2.5 cm/1 inch in length (23 gauge) was used to ensure proper intramuscular injection.

One dose (0.5 ml) contained the following components:

| HEMAGGLUTININ FROM THREE INFLUENZA STRAINS | |
|---|---|
| A/NEW CALEDONIA/20/99 | 15.0 μg |
| A/PANAMA/2007/99 | 15.0 μg |
| B/JOHANNESBURG 5/99 | 15.0 μg |
| THIOMERSAL PRESERVATIVE | 50.0 μg |

Results

The mean age of the total cohort at the time of vaccine administration was 70.4±6.2 years Standard Deviation (S.D.), the female/male ratio was 1.7:1.

Immunogenicity results: Analysis of derived immunogenicity variables was as follows:

| Variable | | Flu-red ID (N = 65) | | | Fluarix ™ IM (N = 65) | | |
|---|---|---|---|---|---|---|---|
| GMT | | GMT | LL | UL | GMT | LL | UL |
| A/NEW CALEDONIA | PRE | 99.5 | 76.9 | 128.7 | 90.0 | 70.1 | 115.7 |
|  | POST | 165.1 | 129.2 | 211.0 | 174.3 | 133.3 | 227.9 |
| A/PANAMA | PRE | 75.5 | 54.7 | 104.2 | 69.2 | 51.9 | 92.4 |
|  | POST | 128.6 | 99.1 | 166.8 | 164.3 | 126.0 | 214.1 |
| B/JOHANNESBURG | PRE | 236.0 | 187.7 | 296.8 | 222.6 | 176.9 | 280.2 |
|  | POST | 341.2 | 276.0 | 421.7 | 402.4 | 312.1 | 518.9 |
| Seroconversion rate | | % | LL | UL | % | LL | UL |
| A/NEW CALEDONIA | | 15.4 | 7.6 | 26.5 | 18.5 | 9.9 | 30.0 |
| A/PANAMA | | 20.0 | 11.1 | 31.8 | 29.2 | 18.6 | 41.8 |
| B/JOHANNESBURG | | 9.2 | 3.5 | 19.0 | 16.9 | 8.8 | 28.3 |
| Conversion factor | | GMR | LL | UL | GMR | LL | UL |
| A/NEW CALEDONIA | | 1.7 | 1.4 | 2.0 | 1.9 | 1.6 | 2.3 |
| A/PANAMA | | 1.7 | 1.4 | 2.1 | 2.4 | 1.9 | 3.0 |
| B/JOHANNESBURG | | 1.4 | 1.2 | 1.7 | 1.8 | 1.5 | 2.1 |
| Seroprotection rate | | % | LL | UL | % | LL | UL |

-continued

| Immunogenicity results: Analysis of derived immunogenicity variables was as follows: | | | | | | | |
|---|---|---|---|---|---|---|---|
| A/NEW | PRE | 87.7 | 77.2 | 94.5 | 90.8 | 81.0 | 96.5 |
| CALEDONIA | POST | 92.3 | 83.0 | 97.5 | 96.9 | 89.3 | 99.6 |
| A/PANAMA | PRE | 75.4 | 63.1 | 85.2 | 81.5 | 70.0 | 90.1 |
| | POST | 90.8 | 81.0 | 96.5 | 93.8 | 85.0 | 98.3 |
| B/ | PRE | 98.5 | 91.7 | 100.0 | 96.9 | 89.3 | 99.6 |
| JOHANNESBURG | POST | 100.0 | 94.5 | 100.0 | 98.5 | 91.7 | 100.0 |

N: number of subjects with available results; %: percentage of subjects within the given parameter;
LL/UL: lower and upper limit of 95% CI; Pre: at the time of vaccine administration; Post: 21 days after the vaccine dose Injection site pain, reported by 10/65 (15.4%) vaccinees, was the most common symptom following IM administration of Fluarix™. In the ID group, pain was reported by 3/65 (4.6%) vaccinees. This difference was statistically significant (p=0.038; Fisher exact test). Accordingly the ID delivery of a thiomersal reduced product is preferred.

Conclusions

Both ID and IM administration of a thio-reduced flu vaccine in an elderly population can provide 100% seroprotection.

A comparable response to vaccination in terms of geometric mean titers, seroprotection rates, seroconversion rates and conversion factors was found in IM and ID vaccinated individuals where the ID group received 2.5-fold less antigen. There was no discernible difference in the overall incidence of vaccine-related solicited/unsolicited systemic symptoms in the two treatment groups.

Example 10

Intradermal Delivery of a Thiomersal-reduced Influenza Vaccine

Immunogenicity of the thiomersal reduced split influenza vaccine prepared as described in Example 9 (except that the pooling was done independently and the vaccine was not filled into syringes) was assessed by ID delivery in guinea pigs using a standard needle.

Groups of 5 animals each were primed intranasally with whole inactivated trivalent influenza virus containing 5 μg of each HA in a total volume of 200 μl. Twenty-eight days after priming the animals were vaccinated by either the intradermal or intramuscular routes. Intradermal doses containing 0.1, 0.3, or 1.0 μg trivalent thiomersal-reduced split Flu in 0.1 ml were administered in the back of the guinea pig using a standard needle An intramuscular dose of 1.0 μg trivalent thiomersal-reduced split Flu was administered in the hind leg of the guinea pig in a volume of 0.1 ml. The groups were as follows:

Group 1—0.1 μg trivalent thiomersal-reduced split Flu ID;

Group 2—0.3 μg trivalent thiomersal-reduced split Flu ID;

Group 3—1.0 μg trivalent thiomersal-reduced split Flu ID

Group 4—1.0 μg trivalent thiomersal-reduced split Flu IM

Fourteen days after vaccination the animals were bled and the antibody titers induced by the vaccination were assessed using a standard hemagglutination inhibition assay (HI). The results are shown in FIG. 1. Strong HI responses to all three strains were induced by vaccination. No clear dose response was noted suggesting that very low doses of thiomersal-reduced antigen can still induce very potent HI antibody responses when administered by the ID route. There was no significant difference between the HI titers induced by ID or IM vaccination. Thus, the results obtained in guinea pigs confirmed that the thimerosal-reduced trivalent split influenza antigens induce similar levels of HI antibodies in animals when delivered by the ID route compared to the IM route.

Example 11

Intradermal Delivery of a Thiomersal-reduced, Adjuvanted Influenza Vaccine

Protocol

Guinea pigs were primed on Day 0 with 5 μg trivalent whole inactivated Flu virus in 200 μl, intranasally.

Vaccination—Day 28—Vaccine containing 0.1 μg HA per strain trivalent split Flu prepared as described in Example 9 (except that the pooling step resulted in a final concentration for each antigen of 1.0 μg/ml to give a dose of 0.1 μg in 100 μl compared to 60 μg/ml in Example 9). The final trivalent formulation was administered intradermally using tuberculin syringes, either adjuvanted or unadjuvanted, in 100 μl.

Bleeding—Day 42.

The effect of adjuvantation was assessed by measuring antibody responses by HI assay (day 0, 28, 42).

All ID experiments were carried out using a standard needle.

Results

G1-G5 refer to 5 groups of guinea pigs, 5 per group.

| | |
|---|---|
| G1 | Split trivalent thiomersal reduced 0.1 μg |
| G2 | Split trivalent thio red 0.1 μg + 3D-MPL 50 μg |
| G3 | Split trivalent thio red 0.1 μg + 3D-MPL 10 μg |
| G4 | Split trivalent thio red 0.1 μg + 3D-MPLin 50 μg + QS21 50 μg |
| G5 | Split trivalent thio red 0.1 μg + 3D-MPLin 10 μg + QS21 10 μg |

Note 3D-MPLin+QS21 refers to an adjuvant formulation which comprises a unilamellar vesicle comprising cholesterol, having a lipid bilayer comprising dioleoyl phosphatidyl choline, wherein the QS21 and the 3D-MPL are associated with, or embedded within, the lipid bilayer. Such adjuvant formulations are described in EP 0 822 831 B, the disclosure of which is incorporated herein by reference.

| | HI Titres anti-A/New Caledonia/20/99 | | |
|---|---|---|---|
| NC | Pre-immun | Pre-boost | Post-boost |
| G1 | 5 | 10 | 92 |
| G2 | 5 | 10 | 70 |
| G3 | 5 | 11 | 121 |
| G4 | 7 | 9 | 368 |
| G5 | 5 | 10 | 243 |

| HI Titres anti-A/Panama/2007/99 | | | |
|---|---|---|---|
| P | Pre-immun | Pre-boost | Post-boost |
| G1 | 5 | 485 | 7760 |
| G2 | 5 | 279 | 7760 |
| G3 | 5 | 485 | 8914 |
| G4 | 7 | 485 | 47051 |
| G5 | 5 | 320 | 17829 |

| HI Titres anti-B/Johannesburg/5/99 | | | |
|---|---|---|---|
| J | Pre-immun | Pre-boost | Post-boost |
| G1 | 5 | 23 | 184 |
| G2 | 5 | 11 | 121 |
| G3 | 5 | 11 | 70 |
| G4 | 6 | 15 | 557 |
| G5 | 5 | 13 | 320 |

Thus, whether adjuvanted or unadjuvanted the thiomersal-reduced trivalent split Flu antigen is a potent immunogen and capable of inducing strong HI responses when administered by the ID or IM route. These responses appear to be at least as potent as the responses induced by the standard Fluarix preparation.

Example 12

Comparison of Thiomersal-containing and Thiomersal-free Vaccine Delivered Intradermally in Pigs In order to assess the immunogenicity of the split Flu vaccine (plus and minus thiomersal) administered by the ID route the primed pig model was used. As the vast majority of the population has experienced at least one infection with influenza an influenza vaccine must be able to boost a pre-existing immune response. Therefore animals are primed in an effort to best simulate the human situation.

In this experiment 4 week old pigs were primed by the intranasal route. Six groups of five animals each were primed as follows:

Group 1—two primings of trivalent whole inactivated virus (50 μg each HA) at day 0 and 14; Group 2—two primings of trivalent whole inactivated virus (50 μg each HA) at day 0 and 14; Group 3—single priming with trivalent whole inactivated virus (50 μg each HA) at day 0; Group 4—two primings of trivalent whole inactivated virus (25 μg each HA) at day 0 and 14; Group 5—single priming of trivalent whole inactivated virus (25 μg each HA) at day 0; Group 6—two primings of trivalent whole inactivated virus (12.5 μg each HA) at day 0 and 14.

On day 28 post final priming, the animals were vaccinated with 3 μg each HA trivalent split antigen (strains A/New Caledonia H1N1, A/Panama H3N2, and B/Johannesburg) in 100 μl by the ID route. Group 1 received standard Fluarix™ containing thiomersal preservative as vaccine antigen. All other groups received the preservative-free antigen.

Figure 2:
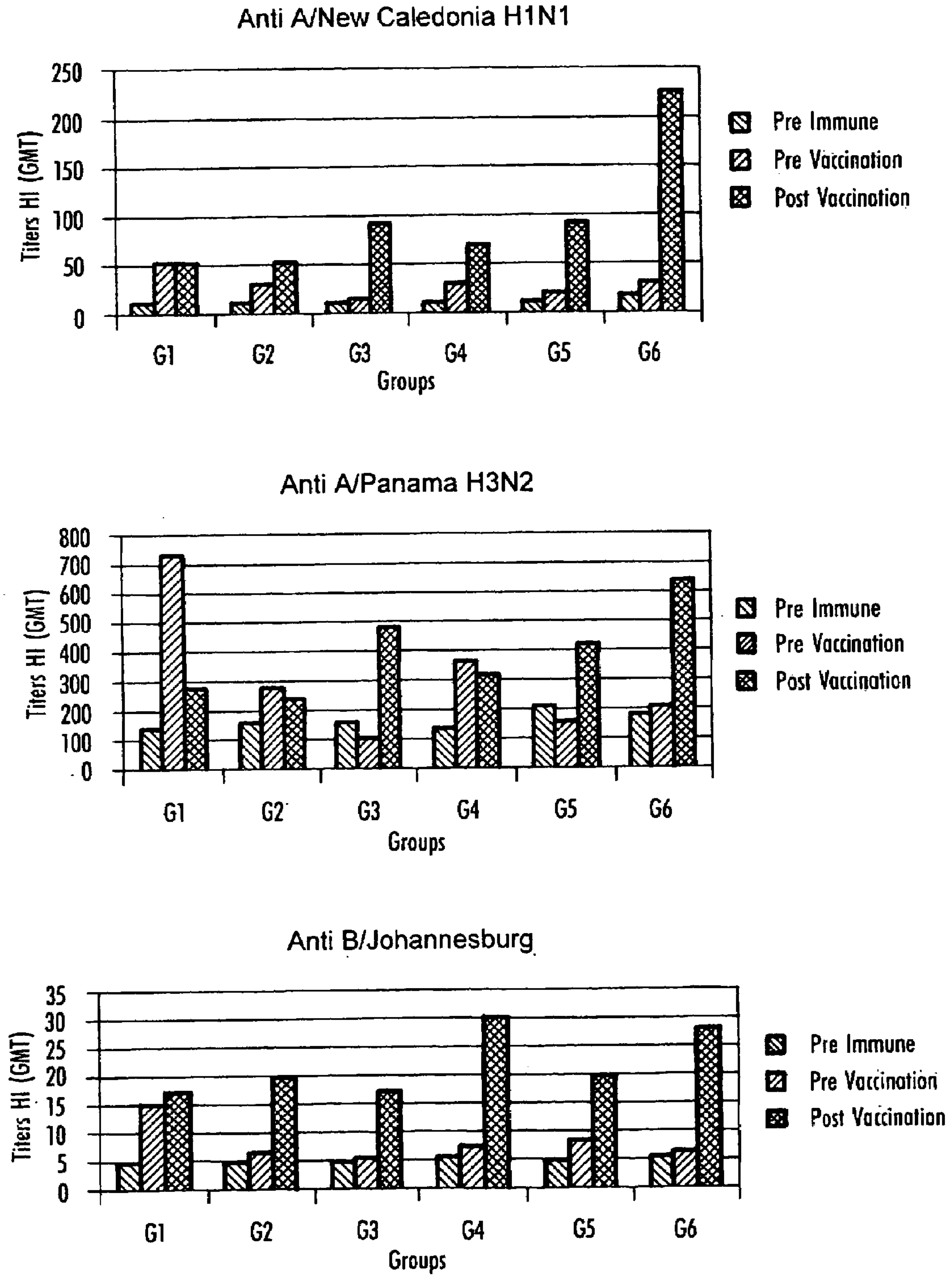
FIG. 2 is the results of the HI (haemagglutinin inhibition) assay done in Example 12.

The HI results obtained in this experiment are shown in FIG. 2 (Anti-Influenza Hemagglutination Inhibition Titers Induced in Pigs Primed with a Variety of Antigen Doses and Vaccinated with 3 Micrograms Trivalent Influenza Antigen Plus or Minus Thiomersal by the Intradermal Route).

Relatively low HI titers are induced to the B strain in this experiment and the background against the A/H3N2 strain is high. A beneficial effect in terms of response to vaccination is observed when the priming dose is reduced. In almost all cases, reduction in the antigen concentration or number of priming doses (from the two primings with 50 μg) resulted in a heightened response to vaccination. While the response of the animals in Groups 1 and 2, which were primed twice with 50 μg, to vaccination is not so evident, it appears that the preservative-free antigen (Group 2) functions at least as well as Fluarix™ (Group 1) under these conditions. A strong response to vaccination with preservative-free trivalent influenza antigen administered by the ID route in the alternatively primed animals (Groups 3-6) is clear and this response is seen even in the B strain, although the HI titers remain low.

I claim:

1. An aqueous, inactivated influenza virus preparation comprising a haemagglutinin antigen (HA) stabilised in the absence of thiomersal, or at a level of thiomersal of 5 μg/ml or less, wherein the HA is detectable by a Single Radial Immunodiffusion (SRD) assay, wherein the preparation comprises α-tocopherol succinate in a sufficient amount to stabilise the HA.

2. The inactivated influenza virus preparation according to claim 1, wherein the α-tocopherol succinate is present at a concentration between 1 μg/ml and 10 mg/ml.

3. The aqueous, inactivated influenza virus preparation according to claim 2, wherein the α-tocopherol succinate is present at a concentration between 10 and 500 μg/ml.

4. The aqueous, inactivated influenza virus preparation according to claim 1, wherein the influenza virus antigen preparation is selected from the group of: split virus antigen preparations, subunit antigens, and chemically or otherwise inactivated whole virus.

5. The aqueous, inactivated influenza virus preparation according to claim 1, wherein the preparation comprises both A and B strain haemagglutinin.

6. The aqueous, inactivated influenza virus preparation according to claim 5, wherein the preparation is a trivalent influenza virus preparation.

7. The aqueous, inactivated influenza virus preparation according to claim 1, wherein the stabilised HA is from an influenza B strain.

8. An influenza vaccine comprising the aqueous, inactivated influenza virus preparation according to claim 1.

9. The influenza vaccine according to claim 8, wherein the concentration of haemagglutinin antigen for each strain of influenza is 1-1000 μg per ml, as measured by a SRD assay.

10. An influenza vaccine according to claim 8, wherein the vaccine additionally comprises an adjuvant.

11. A method for preparing the aqueous, inactivated influenza virus preparation of claim 1 which method comprises purifying the antigen in the presence of α-tocopherol succinate.

12. A method for prophylaxis of influenza infection or disease in a subject which method comprises administering to the subject a vaccine according to claim 8.

13. A method according to claim 12, in which vaccine delivery is intradermal, intranasal, intramuscular, oral or subcutaneous.

14. The aqueous, inactivated influenza virus preparation according to claim 1, wherein said influenza virus is a split influenza virus.

15. The aqueous, inactivated influenza virus preparation according to claim 2, wherein said influenza virus is a split influenza virus.

16. The aqueous, inactivated influenza virus preparation according to claim 3, wherein said influenza virus is a split influenza virus.

* * * * *